United States Patent [19]

Zaschke et al.

[11] 4,438,268
[45] Mar. 20, 1984

[54] LIQUID CRYSTAL SUBSTANCES

[76] Inventors: Horst Zaschke, Plectz der Volkerfreundschaft 3, 4020 Halle; Wolfgang Schafer, auf dern Viewitt 31, 1500 Potsdam; Hans-Joachim Deutscher, Veszpremerstr. 15, 4020 Halle; Dietrich Demus, Valchonweg 22, 4020 Halle; Gerhard Pelzl, Block 170/2/21, 4020 Halle, all of German Democratic Rep.

[21] Appl. No.: 302,288

[22] Filed: Sep. 14, 1981

[30] Foreign Application Priority Data

Sep. 29, 1980 [DD] German Democratic Rep. ... 224159
Sep. 29, 1980 [DD] German Democratic Rep. ... 224160

[51] Int. Cl.³ ............. C07C 69/753; C07D 239/26; C07D 239/28; C09K 3/34
[52] U.S. Cl. .................... 544/315; 260/463; 260/465 D; 252/299.61; 252/299.62; 252/299.63; 560/59; 560/61; 560/73; 560/118; 560/119; 544/316; 544/318; 544/334; 544/335; 544/383; 544/392; 544/394; 544/395
[58] Field of Search ............ 252/299.61, 299.62, 252/299.63; 260/465 D, 463; 560/118, 119, 59, 61, 73; 544/315, 316, 318, 298, 334, 335, 383, 394, 392, 395

[56] References Cited

U.S. PATENT DOCUMENTS

| T901,017 | 8/1972 | Hamb et al. | 585/20 |
|---|---|---|---|
| 3,594,436 | 7/1971 | Hedge et al. | 585/20 |
| 4,119,558 | 10/1978 | Coates et al. | 252/299.62 |
| 4,340,498 | 7/1982 | Sugimori | 252/299.67 |

FOREIGN PATENT DOCUMENTS

| 25598 | 3/1981 | European Pat. Off. | 252/299.62 |
|---|---|---|---|
| 2949080 | 6/1981 | Fed. Rep. of Germany | 252/299.62 |
| 49-35370 | 4/1974 | Japan | 585/20 |
| 56-46855 | 4/1981 | Japan | 252/299.62 |
| 56-108740 | 8/1981 | Japan | 252/299.62 |
| 2082179 | 3/1982 | United Kingdom | 252/299.62 |
| 2084576 | 4/1982 | United Kingdom | 252/299.62 |
| 2090593 | 7/1982 | United Kingdom | 252/299.62 |

OTHER PUBLICATIONS

Lauk, U., et al., Helvetica Chimica Acta, vol. 64, FASC 6, No. 176, pp. 1847–1848, (1981).
Coates, D., et al., Mol. Cryst. Liq. Cryst., vol. 37, pp. 249–262, (1976).
Coates, D., et al., Mol. Cryst. Liq. Cryst., vol. 41, (Letters), pp. 119–124, (1978).

Primary Examiner—Teddy S. Gron
Attorney, Agent, or Firm—Jordan and Hamburg

[57] ABSTRACT

This invention relates to new nematic liquid crystal substances for electro-optical components.

The object of this invention is to create substances for electro-optical components combining chemical and thermal stability with low melting and high clear points at low operational voltage, as well as to processes for their production.

It has been found that new liquid-crystal trans-6-n-alkyl-decalin-2-carbonic acid ester of the general formula

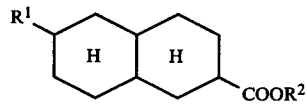

can be introduced into electro-optical components.

These substances are produced by the catalytic high-pressure hydrogenation of 6-n-alkylnaphthalene-2-carbonic acids, separation of the trans-isomers by distillation, and esterification with the corresponding hydroxy compounds of the acyl chlorides obtained through reaction with thionyl chloride.

12 Claims, No Drawings

LIQUID CRYSTAL SUBSTANCES

BACKGROUND OF THE INVENTION AND PRIOR ART STATEMENT

This invention relates to new nematic liquid-crystal substances for electro-optical components for the modulation of incident or traversing light as well as for the representation of numerals, signs and images as well as to processes for their manufacture.

Electro-optical components on the basis of twisted layers (Schedt-Helfrich cells) or on the basis of guest-host effects require nematic liquid crystals with a high positive dielectric anisotropy, low melting and high clear temperatures. Depending on the activation variant, certain values of optical anisotropy, of electro-optical characteristics and of viscosity constants are required, as well as elastic constants. There is no pure substance which fulfills all requirements. For this reason without exception, mixtures whose composition is adjusted to the particular requirements of each situation also employed. To vary the qualities of these mixtures, a conceivably wide range of different substances is needed, possibly from different classes of substances, in order to leave enought latitude for a change in characteristics of the mixtures of substances. For this reason, there is an ongoing search for new liquid crystals with favorable qualities.

The prior art merely describes unsubstituted decalin carbonic acids. The nonmesogeneous cis-decalin-2-carbonic acid is generated as the principal product through the hydrogenation of naphthalin-2-carbonic acid with platinum dioxide in glacial crystalline acetic acid at 240 at, (W. Dauben, E. Hoerger, J. Amer. Chem. Soc. 73, 1504 (1951)). All hydrogenation tests conducted with Raney-nickel in an alkaline medium under high pressure led to 5,6,7,8-tetrahydronaphthalene-2-carbonic acid (G. Stork, J. Amer. Chem. Soc. 69, 576 (1947)). It was only possible to synthesize the trans-decalin-2-carbonic acid from trans-decalin through chlorination and subsequent Grignard reaction, which produced a low yield (1. N. B. Chapman, J. Shorter, K. J. Toine, J. Chem. Soc. 1964, 1077. 2. W. Dauben, R. Tweit, J. Amer. Chem. Soc. 76, 3197 (1954)).

The object of the invention is to create substances for electro-optical components which combine chemical and thermal stability with low melting and high clear points at low operating voltage, as well as to the processes for their preparation.

SUMMARY OF THE INVENTION

It was found that new liquid-crystal trans-6-n-alkyl-decalin-2-carbonic acid ester of the general formula

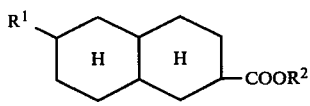

wherein $R^1 = -C_nH_{2n+1}$

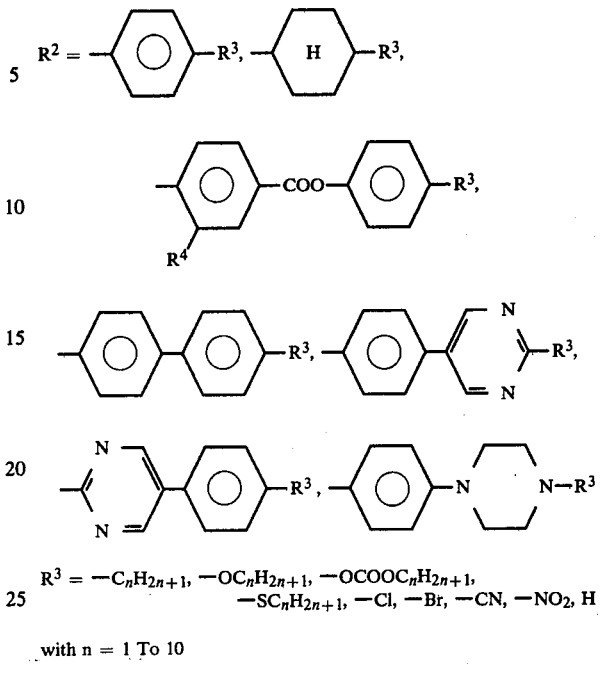

$R^3 = -C_nH_{2n+1}, -OC_nH_{2n+1}, -OCOOC_nH_{2n+1}, -SC_nH_{2n+1}, -Cl, -Br, -CN, -NO_2, H$ with n = 1 To 10

$R^4 = -H, Cl, -C_2H_5$ can be used in electro-optical components for the modulation of incident or traversing light as well as for the representation of numerals, signs and images. The compounds of this invention are chemically and thermally stable and, in part, have high clear points and a strongly positive dielectric anistropy.

DETAILED DESCRIPTION OF THE PREFERRED EMBODIMENTS

It has been found that the liquid crystal trans-8-n-alkyldecalin-2-carbonic acid ester can be produced through the catalytic high-pressure hydrogenation of 6-n-alkylnaphthalene-2-carbonic acids, separation of the trans-isomers through distillation, and esterification of the acyl chloride obtained through a reaction with thionyl chloride with the corresponding hydroxy compounds.

The naphthalene compounds required as starting substances can be produced by a known process (D. Coates and G. W. Gray, Mol. Cryst. Liqu. Cryst. 37, 249 (1976)). According to this process, 6-n-alkynaphthalene-2-carbonic acids are obtained through Friedel-Crafts acylation of naphthalene, followed by a reduction of the ketone by hydrazine hydrate according to Huang-Minlou, with repeated Friedel-Crafts acylation with acetyl chloride or acetane hydride of the resultant 2-n-acylnaphthalene and oxidation of 6'-n-alkyl-2'-acetonaphthone by alkali hypobromide.

The invention will now be explained in more detail by way of examples.

EXAMPLE 1

The following Tables 1 and 2 list the conversion temperatures of the substances according to the present invention.

TABLE 1

[Structure: H9C4-decalin-C(=O)-O-phenyl(R4)-C(=O)-O-phenyl-R3]

| R4 | R3 | K | | S | | N | | I | |
|----|----|----|----|----|----|----|----|----|----|
| H | $OC_4H_9$ | . | 70–71 | . | 139–140 | . | 246–249 | . | |
| H | $OC_7H_{15}$ | . | 62–63 | . | 159–160 | . | 215–216 | . | |
| Cl | $OC_7H_{15}$ | . | 78–80 | — | | — | | . 200.5 | . |
| H | $C_5H_{11}$ | . | 67–69 | . | 150–151 | . | 222–224 | . | |
| H | CN | . | 100–101 | — | | — | | . 294–296 | . (Decomp.) |

K = crystalline-solid
S = smectic
N = nematic
I = isotropic-liquid

TABLE 2

6-n-alkyldecalin-2 carbonic acid 4-subst.-biphenylester and analogous esters

[Structure: $H_9C_4$-decalin-COO—$R^2$]

| $R^2$ | $R^3$ | K | | N | | I |
|---|---|---|---|---|---|---|
| —⌬—⌬— (biphenyl) | H | . | 61–63 | — — | . | 164–166 . |
| —⌬—⌬— (biphenyl) | Br | . | 126–128 | . 177–179 | . | 266–267 . |
| —⌬—pyrimidine | $C_5H_{11}$ | . | 93–94 | — — | . | 218–219 . |
| —⌬—pyrimidine | CN | . | 104–105 | . 208–209 | . | 237–238 . |
| pyrimidine—⌬— | $OC_9H_{19}$ | . | 65–66 | . 189–190 | — | — . |
| —⌬— (phenyl) | CN | . | 97 | — — | — | — . |

EXAMPLE 2

The nematic mixture of the following composition $C_3H_7$—⌬(H)—COO—⌬—CN    31.05 Mol-%

$C_4H_9$—⌬(H)—COO—⌬—CN    27.90 Mol-%

-continued $C_5H_{11}$—⌬(H)—COO—⌬—CN    31.05 Mol-%

$C_4H_9$—decalin(H,H)—COO—⌬—COO—⌬—CN    10 Mol-% melts between 8.5 and 16° C. and changes from a nematic into an isotropic liquid between 96.5 and 99° C. The threshold voltage of a twist cell is 1.6 volts.

EXAMPLE 3

Manufacture of 6-n-butyldecalin-2-carbon acid 34 g (0.15 mol) 6-n-butylnaphthalene-2-carbonic acid, together with 20 g KOH in 180 ml water and 10 g Raney-nickel-catalyst, is hydrogenated at 14 MPa and temperatures between 200° and 260° C. for 100 hours in the vibrating autoclave. The potassium salt of the decalin carbonic acid accumulates as foam. The crude acid deposits as a light-yellow oil on the solution after boiling for two hours with conc. HCl. This is taken up in ether, dried over Na$_2$SO$_4$ and fractionally distilled. Cl.P.: 172° C./40 Pa; Yield 60 to 70% of theoretical. The remaining 6-n-butyldecalin-2-carbonic-acids were produced in an analogous manner in that the corresponding 6-n-alkylnaphthalene-2-carbonic-acids were inserted on hydrogenation.

EXAMPLE 4

Manufacture of 6-n-butyldecalin-2-carbonic-acid chloride 23.8 g (0.1 mol) 6-n-butyldecalin-2-carbonic-acid is reacted with a 5-fold amount of thionyl chloride (40 ml). After the addition of 100 ml ether and a few drops of pyridine, the compound is subjected to a slow reflux boiling for 8 hours. Fractionation is carried out after decanting the ether and the remaining thionyl chloride.

Cl. P.: 126° to 128° C./40 Pa; Yield: 80 to 90% of theoretical. The other 6-n-alkyldecalin-2-carbonic acid chlorides are obtained in the same manner with the use of corresponding acids.

EXAMPLE 5

Manufacture of 4-(6-n-alkyldecalin-2-carbonyloxy)-benzoic-acid-4-'subst. phenylester The requisite 4-hydroxybenzoic-acid-phenylester is obtained by following the teachings of the existing technical literature (J. P. van Meter, B. H. Klanderman, Mol. Cryst. 22, 235 (1973)).

4-hydroxybenzoic acid-p-cyanophenylester is obtained through the esterification of benzyloxycarbonyloxybenzoyl chloride with 4-cyanophenol and subsequent catalytic splitting of the protective group through hydrogen in the presence of Pb/SrCO$_3$ as a catalyst.

The following new variant exhibits even more success when employed for the synthesis of substituted 4-hydroxybenzoic-acid-phenylesters: 8 g (0.023 mol) 4-n-butyldecalin-2-carbonic-acid-4'-formyl-phenylester is dissolved in 20 ml 90% acetic acid. 5 g CrO$_3$ in 10 ml 60% acetic acid is added, drop by drop to this, the mixture then being stirred for 12 hours at 40° C. After cooling off, 50 ml water are added, the deposited precipitate is introduced into ether, the ether extract is washed with water and a solution of bicarbonate, and then dried over Na$_2$SO$_4$. After removal of the solvent, the solid crude acid is reduced to the acid chloride without further purification.

Esterification is processed according to the variant of
EINHORN 0.005 mol of the corresponding substituted phenol or 4-hydroxybenzoic-acid-phenylester in 20 ml pyridine is mixed with an equimolar amount of 6-n-alkyldecalin-2-carbonic-acyl chloride or 4-(6-n-alkyldecalin-2-carbonyloxy)-benzoyl chloride. The preparation is left standing overnight, and subsequently heated for 30 minutes at 70° C. After cooling off, it is poured over 60 g ice and 13 ml conc. sulphuric acid, the deposited precipitate is suctioned off, and the preparation washed in an aqueous bicarbonate solution, water, dilute hydrochloric acid, and again in water. After 3 to 5 recrystallizations from absolute methanol or ethanol, the melting and clear points of the ester are obtained in a pure state.

The yields are between 30 and 70% of the theoretical. The substituted phenyl- and cyclohexyl esters are not mesomorphous.

EXAMPLE 6

Further esters of 6-n-alkyldecalin-2-carbonic acids are obtained, if esterification in processed with hydroxybiphenyl and other analogous hydroxy compounds according to Example 4.

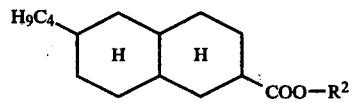

We claim:
1. A liquid crystal trans-6-n-alkyldecalin 2-carbonic acid ester of the general formula

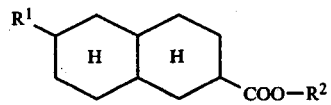

wherein R$^1$=C$_4$H$_9$,

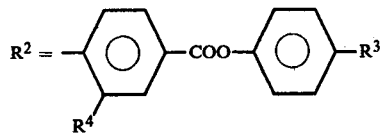

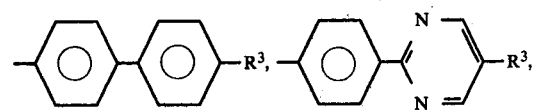

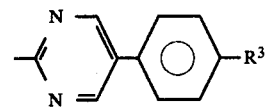

R$^3$ = C$_5$H$_{11}$, —OC$_n$H$_{2n+1}$, —Cl, —Br, —CN, —H with
n=4 to 9
R$^4$=—H, —Cl.
2. A liquid crystal substance according to claim 1, characterized in that R$^1$=C$_4$H$_9$

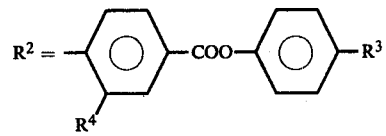

R$^3$ = OC$_4$H$_9$ AND R$^4$ = —H, WHICH IS

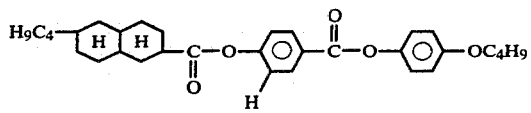

3. A liquid crystal substance according to claim 1, characterized in that $R^1 = C_4H_9$

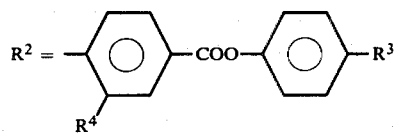

$R^3 = -OC_7H_{15}$ AND $R^4 = $ H, WHICH IS

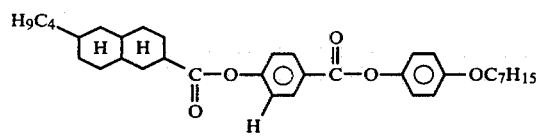

4. A liquid crystal substance according to claim 1, characterized in that $R^1 = C_4H_9$

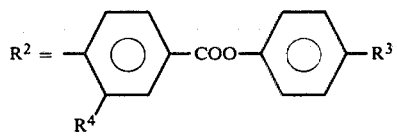

$R^3 = OC_7H_{15}$ AND $R^4 = $ Cl, WHICH IS

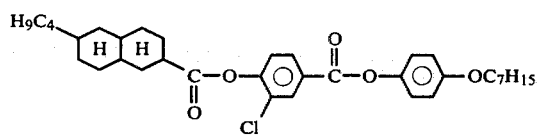

5. A liquid crystal substance according to claim 1, characterized in that $R^1 = C_4H_9$

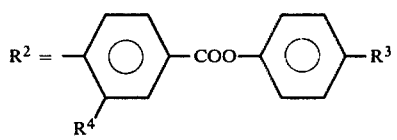

$R^3 = C_5H_{11}$ AND $R^4 = $ H, WHICH IS

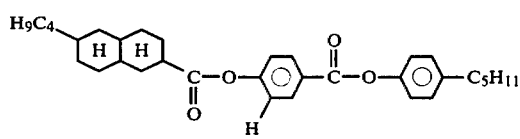

6. A liquid crystal substance according to claim 1, characterized in that $R^1 = C_4H_9$

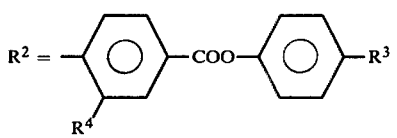

$R^3 = $ CN AND $R^4 = $ H, WHICH IS

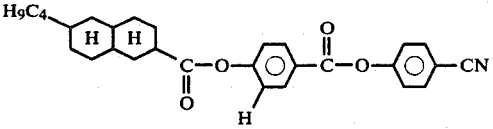

7. A liquid crystal substance according to claim 1, characterized in that $R^1 = C_4H_9$

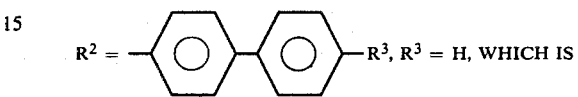

$R^3$, $R^3 = $ H, WHICH IS

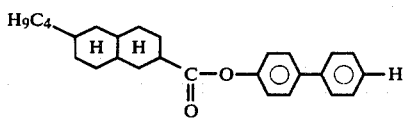

8. A liquid crystal substance according to claim 1, characterized in that $R^1 = C_4H_9$

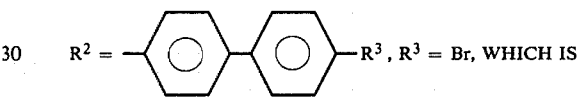

$R^3$, $R^3 = $ Br, WHICH IS

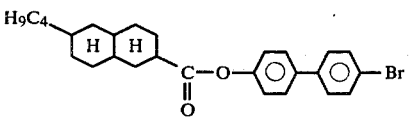

9. A liquid crystal substance according to claim 1, characterized in that $R^1 = C_4H_9$

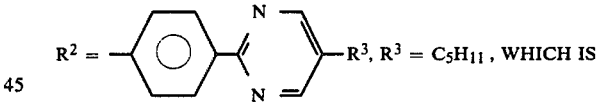

$R^3$, $R^3 = C_5H_{11}$, WHICH IS

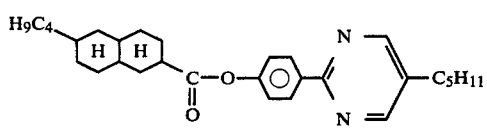

10. A liquid crystal substance according to claim 1, characterized in that $R^1 = C_4H_9$

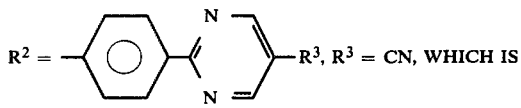

$R^3$, $R^3 = $ CN, WHICH IS

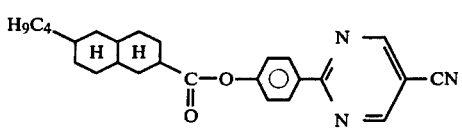

11. A liquid crystal substance according to claim 1, characterized in that $R^1 = C_4H_9$ $R^2 =$ 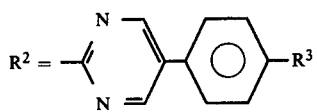
$R^3 = OC_9H_{11}$, WHICH IS
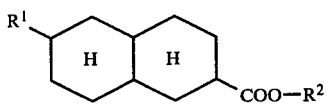
12. A liquid crystal trans-6-n-alkyldecalin-2-carbonic acid ester of the general formula
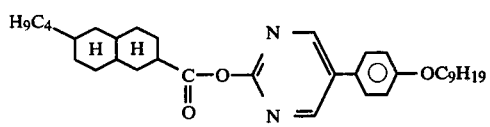
wherein $R^1 = C_nH_{2n+1}$
$R^2 =$ 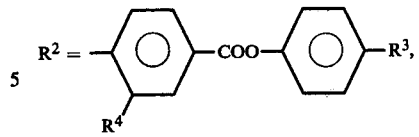
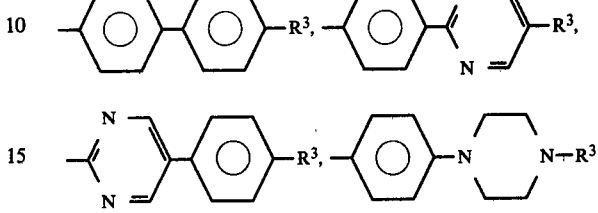
$R^3 = -C_nH_{2n+1}, -OC_nH_{2n+1}, -OCOOC_nH_{2n+1}, -SC_nH_{2n+1},$
$-Cl, -Br, -CN, -NO_2, -H,$
with
 n = 1 to 10
 $R^4 = -H, -Cl, -C_2H_5$.
* * * * *